(12) United States Patent
Davis et al.

(10) Patent No.: US 7,459,012 B2
(45) Date of Patent: Dec. 2, 2008

(54) SOLUTION AND METHOD FOR SCAVENGING SULPHUR COMPOUNDS

(75) Inventors: Stephen Lee Davis, Mill Bay (CA); William Dale Storey, Lacombe (CA)

(73) Assignee: Diversified Industries Ltd., Red Deer (CA)

( * ) Notice: Subject to any disclaimer, the term of this patent is extended or adjusted under 35 U.S.C. 154(b) by 265 days.

(21) Appl. No.: 10/500,134

(22) PCT Filed: Dec. 24, 2002

(86) PCT No.: PCT/CA02/02003

§ 371 (c)(1),
(2), (4) Date: Dec. 1, 2004

(87) PCT Pub. No.: WO03/055578

PCT Pub. Date: Jul. 10, 2003

(65) Prior Publication Data
US 2005/0109210 A1    May 26, 2005

(30) Foreign Application Priority Data
Dec. 28, 2001    (CA)    .................................... 2366470

(51) Int. Cl.
*B01D 53/14*    (2006.01)
(52) U.S. Cl. ........................... 95/235; 95/236; 423/228; 210/634
(58) Field of Classification Search ................. 252/364, 252/60; 423/228; 55/43, 48; 210/634, 660; 95/235, 236
See application file for complete search history.

(56) References Cited

U.S. PATENT DOCUMENTS

| 2,723,221 | A | * | 11/1955 | Stark | ........................... 208/277 |
| 4,007,262 | A | * | 2/1977 | Bowers | ..................... 424/76.7 |
| 4,971,607 | A | * | 11/1990 | Gazzi et al. | ................... 95/174 |
| 5,174,973 | A | | 12/1992 | Smith et al. | |

(Continued)

FOREIGN PATENT DOCUMENTS

EP        0 882 485 A2    12/1998

OTHER PUBLICATIONS http://www.cheltec.com/products.htm.*

(Continued)

*Primary Examiner*—Duane Smith
*Assistant Examiner*—Ives Wu
(74) *Attorney, Agent, or Firm*—Bennett Jones LLP

(57) ABSTRACT

There is disclosed herein a solution for removing a sulphur compound or carbon dioxide from a fluid and methods for its use, said solution comprising sulphuric acid, a metal at between about 0.05 to 10 percent by weight, an amine at between about 10 to 80 percent by volume and water. In one aspect, the sulphuric acid is in the form of a chelating agent and in another it is in the form of a derivative of a sulphur-based acidic compound. The sulphur compound may be hydrogen sulphide, carbonyl sulphide or a mercaptan. In one aspect, the method is practiced at temperatures significantly below zero. In another aspect, this invention is an acid/amine solution comprising sulphuric acid, sulphuric acid in the form of a chelating agent, or a derivative of a sulphur-based acidic compound and monoethanolamine. This solution may be used as a source of monoethanolamine.

29 Claims, 1 Drawing Sheet

A.

B.

U.S. PATENT DOCUMENTS

| | | | |
|---|---|---|---|
| 5,219,542 A | | 6/1993 | Lowery et al. |
| 5,231,063 A | * | 7/1993 | Fukumoto et al. ............ 502/62 |
| 5,395,585 A | | 3/1995 | Goldstein |
| 5,688,478 A | | 11/1997 | Pounds et al. |
| 5,700,438 A | * | 12/1997 | Miller ........................ 423/228 |
| 5,705,135 A | | 1/1998 | Deberry et al. |
| 6,432,375 B1 | | 8/2002 | Dalla Lana et al. |

OTHER PUBLICATIONS

Derwent Publications Ltd., London, GB; AN 1995-183809 XP002239658 & RU 2 021 004 C (Belo Kirova Techn. Inst. (BEKI)), Oct. 15, 1995 abstract.

* cited by examiner

SOLUTION AND METHOD FOR SCAVENGING SULPHUR COMPOUNDS

FIELD OF THE INVENTION

This invention relates to a solution that can be used in removing hydrogen sulphide, mercaptans, carbonyl sulphide and carbon dioxide from gases and liquids.

BACKGROUND OF THE INVENTION

Hydrogen sulphide is a colorless gas, with an odor of rotten eggs. It is produced by bacterial action during the decay of both plant and animal protein and can be formed wherever elemental sulphur or certain sulphur-containing compounds come into contact with organic materials at high temperatures. In industry, it is usually an unintended byproduct, for example from the production of coke from sulphur-containing coal, from the refining of sulphur-containing crude oils, the production of disulphide, the manufacture of vicos rayon, and in the Kraft process for wood pulp.

Natural gases with high concentrations of hydrogen sulphide are known as "sour gases". Hydrogen sulphide in sour gas and crude oil streams is separated during the "sweetening" process. The most widely used sweetening processes in the industry are the amine processes, which use a solution of water and a chemical amine to remove carbon dioxide and several sulphur compounds.

Hydrogen sulphide is also a byproduct of wastewater from treatment plants or water from agricultural practices. Additionally, hydrogen sulphide can be responsible for the unpleasant odor from liquids used in janitorial processes, RV holding tanks, portable toilets and the like. If the emission of hydrogen sulphide from these liquids can be controlled, then the unpleasant odors may be eliminated.

Hydrogen sulphide is toxic to humans and other animals, and represents a significant threat to public safety and health. It can cause serous health risks, most notably in the oil and gas, livestock, waste management and janitorial industries. At 200 parts per million, humans can no longer smell the gas, and therefore can no longer detect it by smell. Higher concentrations than this can cause nausea and headaches. At 500 to 1,000 parts per million, it causes unconsciousness, with death following in two to twenty minutes unless the victim is removed from the area of exposure immediately.

There is a need for a simple, economical and effective means of capturing hydrogen sulphide gas that is present in other gases, or in liquids.

SUMMARY OF THE INVENTION

This invention provides a solution that can be used to remove hydrogen sulphide from gases and liquids, and methods for its use. The solution and methods of this invention can also be used to remove, from gases and liquids, other sulphur compounds, such as carbonyl sulphide, mercaptans, including methyl mercaptan, ethyl mercaptan, n-propyl mercaptan and/or iso-butyl mercaptan. Additionally, the solution and methods of this invention can be used to remove carbon dioxide from gases and liquids, particularly in cold temperatures.

Accordingly, in one aspect the invention is a solution for removing a sulphur compound or carbon dioxide from a gas or a liquid, said solution comprising:
(a) sulphuric acid, at between about 0.1 to 10 percent by volume of the solution;
(b) a metal, at between about 0.05 to 10 percent by weight of the solution;
(c) an amine at between about 10 to 80 percent by volume of the solution; and
(d) water.

In one embodiment the sulphuric acid is in the form of a chelating agent. In one embodiment, the sulphuric acid is present at between about 0.1 to 2 percent by volume of the solution. In one embodiment, the metal is between about 1 to 5 percent by weight of the solution.

In another aspect, the invention is a solution for removing a sulphur compound or carbon dioxide from a gas or a liquid, said solution comprising:
(a) a metal/acid mixture at between about 25 to 75 percent by volume of the solution, said metal/acid mixture comprising:
  (i) sulphuric acid in the form of a chelating agent, at about 2 percent by volume,
  (ii) a metal, at between about 1 to 10 percent by weight, and
  (iii) water; and
(b) an amine at between about 10 to 80 percent by volume of the solution, and
(c) water.

In one embodiment, the metal/acid mixture is present at between about 25 to 50 percent by volume of the solution. In one embodiment the metal is present at between about 1 to 5 percent by weight of the solution.

In another aspect, this invention is a solution for removing a sulphur compound or carbon dioxide from a gas or a liquid:
(a) a derivative of a sulphur-based acidic compound at between about 0.5 to 10 percent by volume of the solution,
(b) a metal, at between about 1 to 10 percent by weight of the solution,
(c) an amine at between about 10 to 80 percent by volume, and
(d) water.

In one embodiment, the derivative of a sulphur-based acidic compound is present at between about 1.25 to 3.75 percent by volume of the solution. In one embodiment the metal is present at between about 1 to 5 percent by weight of the solution.

In the above aspects the sulphur compound may be hydrogen sulphide, methyl mercaptan, ethyl mercaptan, n-propyl mercaptan, iso-butyl mercaptan and/or carbonyl sulphide. In various embodiments of the above aspects, the metal is copper, zinc, or a mixture of copper and zinc. In other embodiments the metal is selected from the group comprising iron, manganese or magnesium, or a mixture thereof. In various embodiments of the above aspects, the amine is monoethanolamine, diglycolamine, methyldiethanolamine, or a mixture of amines. In one embodiment, the amine is present at between about 25 to 50 percent by volume of the solution.

In another aspect, this invention is a solution for removing a sulphur compound from a fluid, said solution comprising:
(a) a derivative of a sulphur-based acidic compound at between about 1.25 to 3.75 percent by volume of the solution
(b) a metal, at between about 1 to 5 percent by weight of the solution,
(c) monoethanolamine at between about 25 to 50 percent by volume of the solution, and
(d) water.

The sulphur compound may be hydrogen sulphide, methyl mercaptan, ethyl mercaptan, n-propyl mercaptan, iso-butyl mercaptan and/or carbonyl sulphide. In one embodiment, the derivative of a sulphur-based acidic compound is at about 2.5 percent by volume of the solution. In one embodiment, the metal is at about 2 to 4 percent by weight. In another, the metal is either copper or zinc. The monoethanolamine may be present at about 25 or 50 percent by volume of the solution.

In another aspect, this invention is a method of removing sulphur compound or carbon dioxide from a fluid, which method comprises:
(a) preparing a solution according to one aspect of this invention, and
(b) contacting the fluid with the solution.

The sulphur compound may be hydrogen sulphide, methyl mercaptan, ethyl mercaptan, n-propyl mercaptan, iso-butyl mercaptan and/or carbonyl sulphide. The fluid may be a gas, such as natural gas, or air. Alternatively, the fluid may be a liquid, such as a liquid hydrocarbon or drilling mud. In one embodiment, this method is practiced at a temperature of between about ° C. and −51° C., and in another at a temperature of between about −10° C. and −40° C.

In another aspect, this invention is a method of removing a sulphur compound or carbon dioxide from a gas, which method comprises:
(a) preparing a solution according to the invention, and
(b) contacting the gas with the solution, and which is characterized in that it is performed at a temperature of between about 0° C. and −51° C., or between about −10° C. and −40° C., −20° C. and −40° C. or −10° C. and −30° C.

In another aspect, this invention is an acid/amine solution comprising:
(a) sulphuric acid, at between about 0.1 to 10 percent by volume of the solution;
(b) monoethanolamine, at between about 10 to 80 percent by volume of the solution; and
(c) water.

In one embodiment, the sulphuric acid is in the form of a chelating agent. In one embodiment, the sulphuric acid is present at between about 0.1 to 2 percent by volume of the solution.

In another aspect, this invention is an acid/amine solution comprising:
(a) a derivative of a sulphur-based acidic compound at between about 0.25 and 10 percent by volume of the solution, and
(b) monoethanolamine at between about 10 to 80 percent by volume of the solution, and
(c) water.

In one embodiment, the derivative of a sulphur-based acidic compound comprises between about 1.25 and 7.5 percent by volume of the solution. In another embodiment, the monoethanolamine comprises between about 25 to 50 percent by volume of the solution.

In yet another aspect, this invention is a solution comprising the acid/amine solution disclosed herein, wherein the acid/amine solution is used as a source of monoethanolamine.

DETAILED DESCRIPTION OF PREFERRED EMBODIMENTS

There is disclosed herein a solution that can be used to remove hydrogen sulphide and other sulphur compounds from gases and liquids, or in any situation where hydrogen sulphide is generated. Particularly, it may be used to remove hydrogen sulphide from natural gas collected from oil and gas wells. "Sulphur compound" as used herein includes hydrogen sulphide, methyl mercaptan, ethyl mercaptan, n-propyl mercaptan, iso-butyl mercaptan and carbonyl sulphide.

The solution of this invention is a mixture of an acid, a metal, an amine and water.

The acid component of the solution is sulphuric acid. Various embodiments of the solution of this invention include sulphuric acid at about 0.5, 0.6 or 1, 2, 3, 4 or 5 percent by volume of the final volume of the solution. In another embodiment, the range of sulphuric acid is between about 0.1 to 2 percent by volume of the final volume of the solution. In yet another embodiment, the range of sulphuric acid is between about 0.1 to 10 percent by volume of the final volume of the solution. When referring to a percentage by volume of sulphuric acid herein, reference is made to a concentrated solution of sulphuric acid that is about 98% sulphuric acid, or about 18 molar sulphuric acid, as can be obtained, for example, from Fisher Scientific.

In one embodiment, the sulphuric acid is in the form of a chelating agent, such as is available from Cheltec, Inc. (U.S.A.), as a product called Stabitrol™. This derivative has the added benefit of having a very low level of corrosiveness to human or animal tissue, while still being a strong acid. Chelate, as used herein means the process that traps and binds certain metal ions to hold them in suspension in liquids. Metal ions that are suspended in liquid will not dissolve as quickly and will bind with bacteria or other metal ions. The feature of chelation is useful because it improves odour control, increases the effectiveness and performance of products such as herbicides and pesticides and permits precious metal extraction without the need for caustic chemicals. "Chelating agent" as used herein refers to a molecule that can chelate metal ions.

One embodiment of the -solution of this invention includes sulphuric acid that is in the form of a chelating agent at a range between about 0.1 to 10 percent by volume of the final volume of the solution. In another embodiment, the range of sulphuric acid in the form of a chelating agent is between about 0.1 to 2.0 percent by volume of the final volume of the solution. In specific embodiments, sulphuric acid in the form of a chelating agent is present at about 0.5, 0.6, 1, 2, 3, 4 or 5 percent by volume of the final volume of the solution. An about 2 percent solution of sulphuric acid in the form of a chelating agent referred to herein, is an about 10-fold dilution of Stabitrol™ or a solution of a substantially chemically equivalent compound.

In another embodiment, the sulphuric acid is a derivative of a sulphur-based acidic compound, such as is available from Cheltec, Inc. (U.S.A.), as a product called Stabitrol™ which is indicated by Cheltec to be a 50 percent derivative of a sulphur-based acidic compound. An about 5 percent by volume solution of a derivative of a sulphur-based acidic compound referred to herein, is a solution of about 10 percent by volume Stabitrol™, or a solution of a substantially chemically equivalent compound. An about 5 percent by volume solution of a derivative of a sulphur-based acidic compound provides a sulphuric acid that is useful in the solution of this invention. In one embodiment, the range of the about 5 percent solution that is used is between about 10 to 75 percent by volume of the solution of this invention, and in another embodiment, between about 25 to 75 percent by volume of the solution. In yet another embodiment, the range of the 5 percent solution that is used is between about 25 to 50 percent by volume of the solution of this invention. In yet another embodiment, the solution comprises up to 10 percent by volume of the derivative of a sulphur-based acidic compound.

The metal component of the solution comprises between about 0.05 to 10 percent by weight of the solution, and exists as a metal ion in solution. In preferred embodiments, the metal component is copper or zinc, however it may be iron, magnesium or manganese. In yet another embodiment, it may be a mixture of any of the above metals. The iron in the solution may be derived from mixing solid iron sulphate with water or another liquid.

In one embodiment the amount of copper in the solution is between about 1 to 99 percent by volume of an about 5 percent by weight solution of copper. In yet another embodiment, the amount of copper in the solution of this invention is between about 25 to 75 percent by volume of an about 5 percent by weight solution of copper. In yet another embodiment, the amount of copper in the solution of this invention is between about 25 to 50 percent by volume of an about 5 percent by weight solution of copper. The copper solution may be derived from mixing solid copper sulphate pentahydrate with water or another liquid. Solid copper sulphate pentahydrate useable in the methods of this invention may be obtained, for example, from HCI Canada Inc., in the form of a solid that is 25.2 percent copper.

In another embodiment the amount of zinc in the solution of this invention is between about 1 to 99 percent by volume of an about 6 to 9 percent by weight solution of zinc. In yet another embodiment, the amount of zinc in the solution of this invention is between about 25 to 75 percent by volume of an about 6 to 9 percent by weight solution of zinc. In yet another embodiment, the amount of zinc in the solution of this invention is between about 25 to 50 percent by volume of an about 6 to 9 percent by weight solution of zinc. The zinc solution may be derived from mixing solid zinc sulphate monohydrate with water or another liquid. Solid zinc sulphate monohydrate useable in the methods of this invention may be obtained, for example, from Tetra Micronutrients, in the form of a solid that is 35.5 to 38 percent zinc.

The amine component of the solution is added as a substantially pure liquid of the amine, or solution of mixed amines. Amines are a colourless, viscous, flammable liquid with a fishy, ammonia-like odor, and they are miscible in water, acetone and methanol. One embodiment of the solution comprises amines in the range of between about 10 to 80 percent by volume of the solution. In another embodiment the solution comprises amines in the range of between about 25 to 75 percent by volume of the solution. On yet another embodiment the solution comprises amines at between about 25 to 50 percent by volume of the solution.

In one embodiment the amine is monoethanolamine, otherwise known as ethanolamine. In other embodiments of the solution other amines, such as diglycolamine (DGA) and methyldiethanolamine (MDEA) or a mixture amines, may be used. The inventors have shown that if the monoethanolamine component of the solution comprises about 2 percent by volume of the final volume of the solution, the solution is stable, meaning that the metal component remains in solution. However, the solution does not work as well at scavenging hydrogen sulphide as when the monoethanolamine component is present at a higher percentage. If the monoethanolamine component of the solution comprises between about 2 and 10 percent by volume of the final volume of the solution, the inventors have shown that solution becomes unstable, in that the metal component will precipitate out of solution. At above 10 percent by volume of monoethanolamine, the solution is once again stable.

The last component of the solution of this invention is water, which may be used to bring the volume of the solution to its desired final volume, or which may already be provided by other components of the solution. One embodiment comprises water at a final volume percentage of between about 20 to 80 percent of the final volume of the solution. Another embodiment comprises water at 25 to 75 percent of the final volume of the solution.

The inventors have shown that various embodiments of the solution of this invention do not freeze at even as low as $-51°$ C. The results of the freezing point analysis are described more fully in Examples 1 and 6 contained herein. The solution can, therefore, be used to remove hydrogen sulphide and other sulphur compounds and other contaminants, in very cold environments. It is noted that the removal of carbon dioxide by this solution appears to be more efficient at cold temperatures than at warmer temperatures, as shown by Example 5. The significant depression of the freezing point was an unexpected result, however it provides the benefit of being able to use this solution at temperatures which would cause other solutions, and in particular other solutions that can be used to scavenge hydrogen sulphide, to freeze. A particularly beneficial use of this solution is in truck scrubbers, as they are used in the field, and may be used at temperatures significantly below freezing. The fact that this solution does not freeze at very low temperatures provides the additional benefit that storage of the solution is simplified, as the potential for the solution to freeze during storage is not a concern. With a freezing point of below $-51°$ C., it is likely that the solution could be used to remove sulphur compounds and carbon dioxide from gases that are at this temperature.

The inventors have also shown in Example 1 disclosed herein, that a solution of 50 percent monoethanolamine: 50 percent of a solution of about 2 percent (v/v) sulphuric acid in the form of a chelating agent (5 percent (v/v) Stabitrol™), will not freeze even as low as $-51°$ C. Example 6 extends these results to show that solutions of 2.5, 10 or 15 percent (v/v) Stabitrol™ and 50 percent (v/v) motoethanolamine, do not freeze even at $-48°$ C. Therefore, this solution may be useful in providing monoethanolamine in a form that can be used at temperatures that would cause monoethanolamine or other monoethanolamine solutions, to freeze. One potential use of this monoethanolamine is in a paint stripper that will be used in cold temperatures.

Having thus disclosed the various components of the solution, an example of how the solution is prepared will now be disclosed. However, this invention is not intended to be limited by the order or method in which the components are mixed together, unless the components cannot be mixed in that order, or by that method, to provide the solution that is disclosed herein. Additionally, this invention is not intended to be limited by the chemicals used in the examples below.

In its broadest aspect, the solution of this invention can be made by mixing together the acid component and water, and then by adding to this mixture, the metal, in either a solid or liquid form. The metal/acid mixture thus formed is then mixed together with the amine component, to form the solution of this invention.

As an example, the inventors first mix the metal and acid together. One method of preparing this metal/acid mixture is to mix 45 gallons of water with 5 gallons of sulphuric acid that is in the form of a chelating agent, for example, Stabitrol™ obtained from Cheltec. Two 50-pound bags of the solid copper sulphate pentahydrate obtained, for example, from HCI Canada Inc., in the form of a solid that is 25.2 percent copper, may then be added while mixing. This metal/acid mixture will therefore comprise about 5 percent by weight copper and about 2 percent by volume sulphuric acid in the form of a chelating agent. Alternatively, it comprises about 5 percent by weight copper and 5 percent by volume of a derivative of a sulphur-based acidic compound. If zinc is the metal component of the solution, solid zinc sulphate monohydrate obtained, for example, from Tetra Micronutrients, in the form of a solid that is 35.5 to 38 percent zinc, is added with mixing, to a final concentration of about 6 to 9 percent zinc by weight.

A metal/acid mixture useful in making the solution of this invention can also be obtained from Cheltec Inc., as a product known as Odorabate™, which is a solution of 2 percent sulphuric acid in the form of a chelating agent and 5 percent copper. Alternatively, a product known as CT-307™ may be obtained from Cheltec, Inc. in the form of a 9 percent zinc chelate. Either of these solutions from Cheltec Inc. can be used as the metal/acid mixture herein.

The metal/acid mixture is then mixed with any additional water, as required to bring the solution to its final volume. Additional water should not be added to the amine component. The metal/acid mixture is then quickly added to the amine component, with mixing to prevent precipitation of the metal. When the metal is zinc, mixing must be particularly vigorous, as zinc will otherwise precipitate out of the solution. The inventors have noticed that the temperature of the solution, upon mixing of the metal/acid mixture with the amine will rise, in some instances up to 120° F., indicating that some type of chemical reaction has occurred. The solution is then allowed to cool before use in the methods of this invention. It should be noted that, if the amine component is present at about 10 percent by volume of the final volume of the solution, or less, the temperature change to 120° F. does not occur, indicating that the presumed chemical reaction between the components from which the solution is made, does not occur.

If the amine component will be less than about 37% by volume of the solution, water should not be added to the amine component before the metaVacid mixture is mixed with the amine. Rather, additional water should be added to the metal/acid mixture first, and then this solution is added to the amine component. More vigorous blending is required in this embodiment of the solution, to ensure that the solution is stable.

One embodiment of the solution comprises about 30 percent by volume of the 5 percent (w/v) copper and 2 percent sulphuric acid in the form of a chelating agent mixture disclosed above; about 16 percent by volume monoethanolamine; about 40 percent by volume ethylene glycol, and about an additional 14 percent by volume water.

One embodiment of the solution comprises about 30 percent by volume of the 5 percent (w/v) copper and 5 percent (v/v) derivative of a sulphur-based acidic compound mixture disclosed above; about 16 percent by volume monoethanolamine; about 40 percent by volume ethylene glycol, and about an additional 14 percent by volume water.

In another embodiment, the solution comprises about 30 percent by volume of the 5 percent (w/v) copper and 2 percent (v/v) sulphuric acid in the form of a chelating agent mixture disclosed above; about 30 percent by volume monoethanolamine, and about 40 percent by volume methanol.

In another embodiment, the solution comprises about 30 percent by volume of the 5 percent (w/v) copper and 5 percent (v/v) derivative of a sulphur-based acidic compound mixture disclosed above; about 30 percent by volume monoethanolamine, and about 40 percent by volume methanol.

In another embodiment, the solution comprises about 30 percent by volume of the 9 percent (w/v) zinc and 2 percent (v/v) sulphuric acid in the form of a chelating agent mixture disclosed above; about 30 percent by volume monoethanolamine, and about 40 percent by volume ethylene glycol.

In another embodiment, the solution comprises about 30 percent by volume of the 9 percent (w/v) zinc and 5 percent (v/v) derivative of a sulphur-based acidic compound mixture disclosed above; about 30 percent by volume monoethanolamine, and about 40 percent by volume ethylene glycol.

In another embodiment the solution comprises about 25 percent by volume of the 5 percent (w/v) copper and 2 percent (v/v) sulphuric acid in the form of a chelating agent mixture disclosed above; about 16.7 percent by volume monoethanolamine, about 41.6 percent by volume ethylene glycol and about an additional 16.7 percent by volume water.

In another embodiment the solution comprises about 25 percent by volume of the 5 percent (w/v) copper and 5 percent (v/v) derivative of a sulphur-based acidic compound mixture disclosed above, about 16.7 percent by volume monoethanolamine, about 41.6 percent by volume ethylene glycol and about an additional 16.7 percent by volume water.

In another embodiment the solution comprises about 50 percent by volume of the 5 percent (w/v) copper and 2 percent (v/v) sulphuric acid in the form of a chelating agent mixture disclosed above and about 50 percent by volume monoethanolamine.

In another embodiment the solution comprises about 50 percent by volume of the 5 percent (w/v) copper and 5 percent (v/v) derivative of a sulphur-based acidic compound mixture disclosed above, and about 50 percent by volume monoethanolamine.

In another embodiment the solution comprises about 50 percent by volume of the 6 percent (w/v) zinc and 2 percent (v/v) sulphuric acid in the form of a chelating agent mixture disclosed above and about 50 percent by volume monoethanolamine.

In another embodiment the solution comprises about 50 percent by volume of the 6 percent (w/v) zinc and 5 percent (v/v) derivative of a sulphur-based acidic compound mixture disclosed above, and about 50 percent by volume monoethanolamine.

In another embodiment the solution comprises about 50 percent by volume of the 9 percent (w/v) zinc and 2 percent (v/v) sulphuric acid in the form of a chelating agent mixture disclosed above and about 50 percent by volume monoethanolamine.

In another embodiment the solution comprises about 50 percent by volume of the 9 percent. (w/v) zinc and 5 percent (v/v) derivative of a sulphur-based acidic compound mixture disclosed above, and about 50 percent by volume monoethanolamine.

In another embodiment the solution comprises about 50 percent by volume of the 5 percent (w/v) copper and 2 percent (v/v) sulphuric acid in the form of a chelating agent mixture disclosed above, 25 percent by volume monoethanolamine and an additional 25 percent by volume water.

In another embodiment the solution comprises about 50 percent by volume of the 5 percent (w/v) copper and 5 percent (v/v) derivative of a sulphur-based acidic compound mixture disclosed above, 25 percent by volume monoethanolamine and an additional 25 percent by volume water.

In another embodiment the solution comprises about 50 percent by volume of the 6 percent (w/v) zinc and 2 percent (v/v) sulphuric acid in the form of a chelating agent mixture disclosed above 25 percent by volume monoethanolamine and an additional 25 percent by volume water.

In another embodiment the solution comprises about 50 percent by volume of the 6 percent (w/v) zinc and 5 percent (v/v) derivative of a sulphur-based acidic compound mixture disclosed above, 25 percent by volume monoethanolamine and an additional 25 percent by volume water.

The pH of the resultant solution will generally be between 8 and 12, but can be adjusted to almost any pH. The inventors have determined that the solution is very efficient at removing hydrogen sulphide when the pH is adjusted to be above 8 and most efficient in the 10 to 11 range. Without being limited to a theory, this is likely the result of the fact that hydrogen sulphide is significantly more soluble at pH 8 than it is at acidic pHs.

Having thus disclosed the solution of this invention and how it is prepared, the methods for using the solution will now be disclosed. In its broadest terms, one method of this invention is to prepare the solution as described, and then to bring the solution into contact with a fluid that contains hydrogen sulphide. The fluid may be a gas or a liquid. As used herein, "gas" means a form of matter that has no fixed volume and will conform in volume to the space available, and is intended to include mixtures of gases, such as air. For example, the gas can be natural gas that contains hydrogen sulphide, it can be air that contains hydrogen sulphide, and which is emitted from wastewater or from agricultural operations, RV holding tanks, or portable toilets, for example. The solution will, upon contact with the hydrogen sulphide-containing gas or air, remove all or a significant portion of, the hydrogen sulphide. Without being limited to a theory, the hydrogen sulphide reacts with the copper, zinc or iron in the solution to form cupric, zinc or iron sulphide, respectively, which are insoluble molecules that precipitate out of the solution.

Alternatively or in addition to hydrogen sulphide, a gas that is used in the methods of this invention may comprise other sulphur compounds. For example, the gas may comprise mercaptans such as methyl mercaptan, ethyl mercaptan, n-propyl mercaptan and/or iso-butyl mercaptan. Alternatively, or in addition, the gas may comprise carbonyl sulphide. The solution will, upon contact with a gas comprising one or more of these sulphur compounds, remove all or a significant portion of these other sulphur compounds from the gas.

Alternatively or in addition, a gas that is used in the methods of this invention may comprise carbon dioxide. The solution of this invention will, upon contact with a gas comprising carbon dioxide, remove a significant portion of the carbon dioxide from the gas. This removal appears to be most efficient at cold temperatures. The solution also appears to have some effect on nitrogen levels.

Figure 1:
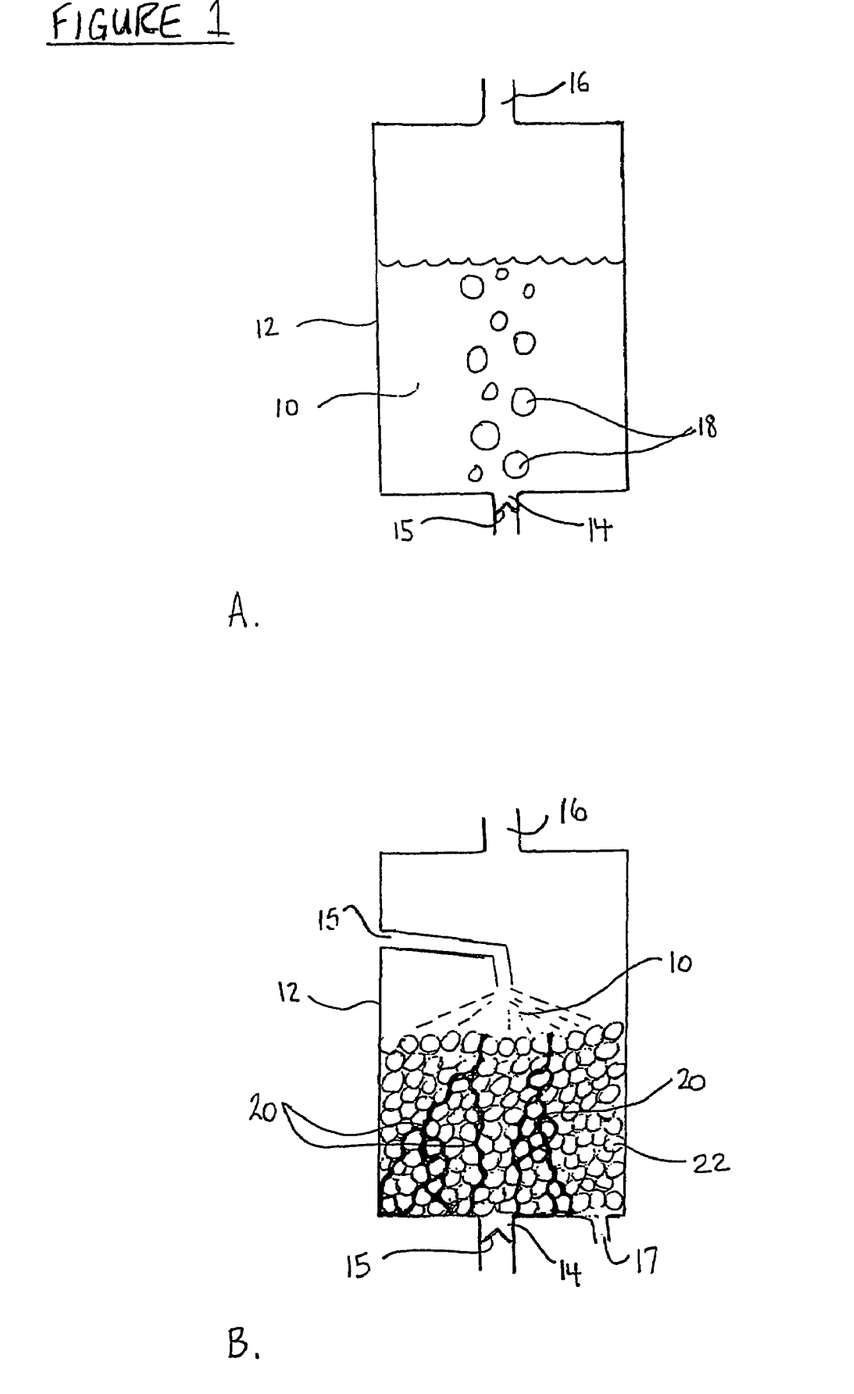
FIG. 1A is a drawing of an apparatus used in the method of this invention.
FIG. 1B is a drawing of another apparatus used in the method of this invention.

FIG. 1A shows one embodiment of the method of this invention in which a gas comprising one or more compounds that are to be removed from the gas is bubbled through a solution of the invention. Examples of the compounds that are to be removed from the gas include, hydrogen sulphide, mercaptans, such as methyl mercaptan, ethyl mercaptan, n-propyl mercaptan and iso-butyl mercaptan, carbonyl sulphide, and carbon dioxide. As seen in FIG. 1, solution 10 is placed into a container 12 that has an entrance opening 14 and an exit opening 16. Entrance opening is fitted with a device 15, such as a one-way valve, that will prevent solution 10 from running out of container 12. The gas 18 enters container 12 through entrance opening 14 and passes through solution 10 by rising upwards because of its low density. Gas 18 exits container 12 through exit opening 16.

As is apparent, the gas 18 moves through solution 10 as a series of bubbles, which increases the surface area of the interaction between solution 10 and gas 18, and causes turbulence in solution 10, both of which increase the efficiency of removal of the desired compounds from gas 18.

FIG. 1B shows another embodiment of the method of this invention, in which solution 10 is passed through tortuous paths 20 in container 12, rather than simply being introduced into container 12 as a volume of liquid. In the method of this embodiment, container 12 again comprises entrance opening 14 and exit opening 16 through which a gas 18 will enter into and exit from container 12. These openings are positioned such that gas 18 must pass through the tortuous paths 20 after entering and before exiting container 12. Additionally, container 12 comprises an opening 15 and an exit 17, through which solution 10 will enter and exit container 12, which are positioned such that solution 10 must pass through the tortuous paths 20 after entering and before exiting container 12. As is apparent, the tortuous paths both increase contact of solution 10 with gas 18, and also provide turbulence to solution 10, both of which increase the efficiency of removal of the compounds from gas 18.

FIG. 1B demonstrates an embodiment of this invention in which the tortuous path is created by introducing a plurality of objects 22, such as small circular balls or "ration rings", into container 12. In one embodiment, these balls are approximately the size of a golf ball. However, balls of different or varying sizes, objects that are not round, but oval or discoid, objects that have rounded and flat edges, or objects with flat edges may be used. Any objects that would function to cause solution 10 and gas 18 to travel around and between them, are intended to be included herein. These objects function to increase the surface area of interaction between the solution 10 and gas 18.

In this embodiment of the method of, this invention, solution 10 is introduced into container 12, in such a way that maximizes its contact with the surface of the objects 22. As demonstrated in FIG. 1B, this may be accomplished by spraying solution 10 over the top surface of the objects, whereafter it will trickle down through the various tortuous paths.

Container 12 may be adapted to collect the gas that exits through exit opening 16, for example to collect natural gas. Alternatively, if the gas 18 is not to be collected, such as after the compounds have been removed from gases emitting from wastewater or from water used in agricultural operations, the gas would be released directly into the atmosphere, presuming it is otherwise clean.

In yet another embodiment of the method of this invention, the solution is mixed with water and misted into a vessel containing gaseous sulphur compounds and carbon dioxide.

In yet another embodiment of this method that is used with steam injection, the solution is injected into steam to react with any sulphur compounds and carbon dioxide that might be in the atmosphere as well as react with any liquids that might be within the tank.

Another embodiment of the method of this invention is to prepare the solution as described, and then to mix the solution with another liquid that contains one or more of hydrogen sulphide, mercaptans, such as methyl mercaptan, ethyl mercaptan, n-propyl mercaptan and iso-butyl mercaptan, carbonyl sulphide or carbon dioxide. When the solution and the liquid are mixed, and without being limited to a theory, the sulphur compounds in the liquid will react with the metal in the solution to form a metal sulphide, an insoluble molecule that precipitates out of the solution. This precipitate can be removed from the mixture, for example by filtration or centrifugation. Alternatively, removal of the precipitate may not be necessary, for instance in a situation where the liquid is a drilling fluid used in oil and gas well drilling.

In particular, the solution may be mixed with liquid hydrocarbons in order to react with naturally occurring sulphur compounds, such as mercaptans. This would be done under temperature and pressure.

In yet another embodiment, drilling mud is mixed with the solution of this invention, in order to remove therefrom a number of compounds including, hydrogen sulphide, carbonyl sulphide, mercaptans such as methyl mercaptan, ethyl mercaptan, n-propyl mercaptan and/or iso-butyl mercaptan, or carbon dioxide.

As disclosed in Example 4, the solution of this invention is not corrosive. The fact that it is not corrosive is of benefit in the handling, use and transport of the solution, as compared to other solutions that may be used for similar purposes and which are corrosive. As well, the solution of this invention is not flammable, it can be diluted in water, and it has a mild odor.

As will be apparent to those skilled in the art, various modifications, adaptations and variations of the preceding and foregoing specific disclosure can be made without departing from the scope of the invention claimed herein. The following examples are intended only to illustrate and describe the invention rather than limit the claims that follow.

EXAMPLES

Example #1

A mixture of 10% Stabitrol™ and 90% water has a freezing point of around 0° C. and a pH of below one. Amine alone has a freezing point of around 0° C. and a pH of between 12-13. The inventors have shown that when 5% Stabitrol™, 45% water and 50% amine are mixed, the solution heats up to about 120° F. during the mixing process, and the freezing point of the final solution is below −51° C. and has a pH of between 10-11. Normally when these chemicals are used independently of one another in cold weather an anti-freeze agent would have to be added. This new mixture eliminates the need for an anti-freeze agent, when using this solution in cold weather.

The percentage of each chemical in this mixture can be varied a great deal, and the resultant mixture will still remain stable, meaning that the metal ion will remain in solution. The percentage of any particular chemical will be based on the application for the mixture, and the pH at which it is required to be effective.

The inventors have made different embodiments of the solution of this invention, in order to determine the freezing point of these various embodiments. A copper/acid mixture, comprising 5% by weight copper and about 2% by volume sulphuric acid in the form of a chelating agent was prepared as described in the detailed description. Additionally an acid solution without copper was prepared, using Stabitrol™. Various amounts of these solutions were then mixed with monoethanolamine, and the freezing point of the solution was measured. The results are provided in Table 1.

TABLE 1

| Copper/Acid Mixture (volume %) | Monoethanolamine (volume %) | Freezing Point |
|---|---|---|
| 25 | 75 | below −51° C. |
| 50 | 50 | below −51° C. |
| 75 | 25 | −18° C. |
| 83.34 | 16.66 | −15° C. |
| Acid Solution (volume %) | | |
| 50 | 50 | below −51° C. |

Additionally, used solution from a test run was subjected to a freezing point analysis, and it was found to freeze at below −51° C.

These results indicate that a solution of acid and amine, or a mixture of acid, amine and metal will have a much lower freezing point than each of the individual liquid components of that solution

Example 2

A series of initial field trials using a mixture of Stabitrol™, water and copper to remove $H_2S$ from gas, were performed. The results of these initial tests were poor, and the inventors believed this to be because the pH was too low, as the pH of this mixture was about one. The inventors hypothesized that the pH of the mixture needed to be at 8 to 10, as the $H_2S$ is much more soluble in a high pH, and therefore there is a much longer contact time between the copper and the $H_2S$.

As the mixture being used for $H_2S$ scavenging should preferably be a liquid in a colder environment, the inventors added an anti-freeze to the Stabitrol™, water and copper mixture, as at the time, they believed the mixture would freeze at around 0° C. When an anti-freeze was added, the results were a little better. However, the inventors found that it was not the anti-freeze that was causing the better results, but rather it was the 2% amine used in the anti-freeze as a corrosion inhibitor, that was making the difference. The solution remained stable with 2% amine mixed into it. Hypothesizing that more amine would be even better at removing $H_2S$, 5% amine was added to the solution. However, when this was done the product became unstable, in that the copper precipitated out of the solution. When 10% amine was added, the mixture heated up and the solution remained stable thereafter. Another series of field trials using new formulas was started.

The next series of tests were done using this Stabitrol™, water, copper, amine and glycol/methanol mixture (as anti-freeze agents). Several different formulas were tested to determine which ones would work the best. There was a wide range of formulas that could be used, and the results were much better than the previous field trials that had been done. The pH of the mixtures generated was between 8 and 11.

The inventors mixed Stabitrol™, water, copper and amine together. Upon mixing these ingredients together the solution heated up to 120° F., indicating that a chemical reaction was occurring. The mixture had a freezing point of below −51° C., therefore by using this mixture there was no need for an anti-freeze to be added. A field trial was run to see if $H_2S$ removal was still effective, and the results were very good.

Continued field trials indicated that there are a wide range of formulas that will yield solutions that are effective as $H_2S$ scavengers. The pH is approximately 10.4 in a 50% (10% (v/v) Stabitrol™, water, 5% (w/v) copper) and 50% amine mixture. It appears that the formula can be varied in many ways, and the final formulations used will depend on the application and climate.

Test #1

20 liters of a solution of: zinc-chelate, (6 liters); monoethanolamine (3.3 liters), glycol (8 liters) and water (2.7 liters), was prepared. 19 liters of this solution was used, but as 2 liters of this was left in the fill hose, only 5.368 liters of the zinc-chelate solution was in tower. The gas had a $H_2S$ content of 8500 ppm. The flooded tower was not reverse circulating. The results are in Table 2. Approximately 5.3 $m^3$ of gas having 8500 ppm $H_2S$, was cleaned with about 5.3 liters of the zinc chelate. These were the best results to date, and considering that the test was done at flow rates of 6 m³ per hour, which is high for this tower, zinc seemed to provide results comparable to those obtained with copper.

TABLE 2

| Time of Day | Meter Reading (m³) | [H₂S] (ppm) | Total m³ through Tower |
|---|---|---|---|
| 9:30 | 103.5 | 0 | 0 |
| 9:45 | 105.2 | 0 | 1.5 |
| 10:00 | 106.7 | 0 | 3.0 |
| 10:15 | 108.2 | 0 | 4.6 |
| 10:22 | 109.0 | 8500 | 5.5 |

Test #2

20 liters of a solution of: Odorabate™ (6 liters), monoethanolamine (6 liters) and methanol (8 liters), was prepared. About 19 liters of product was tested. The gas had H₂S content of 8500 ppm. The flooded tower was packed with ration rings and was not reverse circulated. The results are in Table 3. About 6.75 m³ of gas having 8500 ppm H₂S, was cleaned.

TABLE 3

| Time of Day | Meter Reading (m³) | [H₂S] (ppm) | Total m³ through Tower |
|---|---|---|---|
| 9:21 | 132.63 | 0 | 0 |
| 9:30 | 132.94 | 0 | 0.61 |
| 9:45 | 133.62 | 0 | 0.99 |
| 10:00 | 134.2 | 0 | 1.57 |
| 10:15 | 134.78 | 0 | 2.15 |
| 10:30 | 135.3 | 0 | 2.67 |
| 10:45 | 135.83 | 0 | 3.2 |
| 11:00 | 136.38 | 0 | 3.75 |
| 11:15 | 136.9 | 34 | 4.27 |
| 11:21 | 137.15 | 54 | 4.54 |
| 11:30 | 137.45 | 88 | 4.82 |
| 11:40 | 137.82 | 134 | 5.19 |
| 11:45 | 138.02 | 169 | 5.39 |
| 11:50 | 138.2 | 199 | 5.59 |
| 11:55 | 138.4 | 244 | 5.79 |
| 12:00 | 138.54 | 270 | 5.93 |
| 12:05 | 138.75 | 341 | 6.12 |
| 12:10 | 138.93 | 372 | 6.3 |
| 12:15 | 139.05 | 421 | 6.42 |
| 12:20 | 139.23 | 750 | 6.6 |
| 12:30 | 139.75 | 4200 | 7.12 |
| 12:40 | 140.08 | 6800 | 7.45 |
| 12:50 | 140.6 | 8500 | 7.97 |

Test #3

20 liters of a solution of monoethanolamine (3.3 liters), ethylene glycol (8 liters) and water (8.7 liters) was prepared. 19 liters of solution was tested. The gas had H₂S content of 8500 ppm. The tower was flooded, the column was packed with ration rings, and it was not reverse circulating. No Stabitrol™ or Odorabate™, or acid/metal solution was used in this test. The results are shown in Table 4. For the first time, vapors were seen coming off of the gas sampling line. After tabulating the total volume of gas, it was calculated that 3.95 m³ of gas was cleaned.

TABLE 4

| Time of Day | Meter Reading (m³) | [H₂S] (ppm) | Total m³ through Tower |
|---|---|---|---|
| 1:00 | 140.35 | 3 | 0 |
| 1:15 | 140.50 | 5 | 0.15 |
| 1:30 | 141.52 | 24 | 1.17 |
| 1:45 | 142.10 | 54 | 1.85 |
| 2:00 | 142.6 | 98 | 2.25 |
| 2:15 | 143.24 | 202 | 2.89 |
| 2:30 | 143.85 | 376 | 3.50 |
| 2:45 | 144.36 | 2000 | 4.0 |
| 3:00 | 144.92 | 6500 | 4.6 |
| 3:15 | 145.48 | 8500 | 5.13 |

Test #4

18 liters of a 50:50 Odorabate™/monoethanolamine solution was prepared. No glycol or methanol was used. The outside temperature was −4° C.; there was 24 psi of pressure on the gas system, and the gas had a H₂S content of 8500 ppm. The tower was flooded and the column was packed with ration rings. About 18 liters of solution was tested. The results are shown in Table 5. About 11.38 m³ of gas with an H₂S content of 8500 ppm was cleaned. Therefore, this blend can clean 1.26 m³ of gas comprising 8500 ppm H₂S. With several of the tests that have been done to date, just before breakthrough of H₂S, the gas flow increased slightly. Perhaps if this did not happen, the total volume of gas cleaned would have been extended for a longer period of time.

TABLE 5

| Time | Meter Reading (m³) | [H₂S] (ppm) | Total m³ through Tower |
|---|---|---|---|
| 3:12 | 145.04 | 0 | 0 |
| 3:30 | 145.67 | 0 | 0.63 |
| 4:00 | 146.7 | 0 | 1.66 |
| 4:30 | 148.0 | 0 | 3.00 |
| 5:00 | 148.7 | 0 | 3.66 |
| 5:30 | 149.62 | 0 | (−8° C.) 4.58 |
| 6:00 | 150.84 | 0 | 5.8 |
| 6:30 | 152.04 | 0 | 7.0 |
| 7:00 | 153.22 | 15 | 8.18 |
| 7:15 | 153.72 | 66 | 8.68 |
| 7:30 | 154.19 | 99 | 9.15 |
| 7:45 | 154.8 | 345 | 9.76 |
| 8:00 | 155.34 | 800 | 10.3 |
| 8:15 | 156.0 | 2000 | 11.00 |
| 8:30 | 156.5 | 3000 | 11.46 |
| 8:45 | 157.0 | 5000 | 12.05 |
| 9:00 | 157.48 | 8500 | 12.44 |

Example 3

Each test was conducted in a test vessel that had a test tower which was four-inches in diameter and 10 feet tall, and included a sparger bar ¾-inches in diameter and about 4 inches long with eight holes, 3/32 inches in diameter, drilled at a 45 degree angle alternately to each side of center. A flow meter was used to measure gas flow and there was a flow line to the flare stack. The gas used in these tests was sour gas. Pressure, temperature, and the H₂S content of the gas varied between tests.

The concentration of the H₂S in the gas used varied because several different oil and gas wells were fed into the test complex. If the operator had problems and shut in some wells, the amount of H₂S in the sample would change, as H₂S content differed from well to well.

When there was pressure on the tower, actual flow rates were considerably higher because the gas was compressed. There are set differentials for pressure. The earlier of these tests did not record any pressure, because it was cold outside and the line to flare was clear plastic, so any blow by could be observed. In the winter, the plastic hose maintained its round structure, and the flow was not restricted. The summary data reported at the end of this section includes a 3 psi pressure factor that was included because of the height of the fluid in the tower.

The later tests were done at a warmer temperature and the flare line collapsed because it was made of plastic, causing back pressure on the system. A pressure of 5 to 10 psi caused considerable differences in actual flow rates. The summary data reported at the end allows for these pressure differences. Pressure in working vessels will keep gas bubbles smaller, allowing for better contact with liquids it is bubbling through.

The results of tests of various solutions are outlined in the tables below. The object of these tests was to determine how long each solution was able to maintain an "H$_2$S Out" (see below) of 0 ppm of H$_2$S. The "breakthrough point" is the point at which "H$_2$S Out" rises above 0 ppm of H$_2$S. "Time" is the time of day when the measurements were recorded. "Flow" is the flow rate of natural gas from an on-site well. "H$_2$S In" is the concentration of hydrogen sulphide in the gas that is entering the tower, and "H$_2$S Out" is the concentration of hydrogen sulphide in the gas that exits the solution in the tower. "Colour" is the colour of the solution near the middle of the solution when it is in the tower. "Fluid level" is the level that the fluid reaches in the tower while the gas is flowing into the tower. All tests used a volume of 10 liters of solution, with the exception of the test shown in Table 12, which used 9 liters of solution.

Test #1

A solution of approximately 30% (w/v) of ammonium hydroxide (Strike Oilfield Services; Univar) was tested using the above methods. The outside temperature was −4° C., testing was done at atmospheric pressure. The flow meter was not working during this test. The results are shown in Table 6.

TABLE 6

| Time | Flow (m³) | H$_2$S In (ppm) | H$_2$S Out (ppm) | Colour | pH | Fluid Level (in) |
|---|---|---|---|---|---|---|
| 12:45 | 1:47 | 1800 | 0 | clear | 14.3 | 40 |
| 12:47 | 1:47 | " | 0 | clear | | |
| 1:03 | " | " | 0 | dark grey | | 80 |
| 1:15 | " | " | 0 | dark grey | | " |
| 1:45 | " | " | 1000 | almost black, and some blue | | |
| | | | | | 10.5 | 31.5 |

Test #2

A solution of 5% (v/v) Stabitrol™; 2.5% (w/v) copper and 50% (v/v) monoethanolamine was tested. The outside temperature was −4° C. and no pressure was applied during the test. The results are shown in Table 7. The solution did not foam during the test. The byproduct of the reaction was very thick, and the use of a sparger bar made this a very efficient tower. The byproduct was centrifuged and the result was approximately 70-80% solids. These solids, when placed in a beaker of water, instantly broke up and dispersed into water. No particles were over 4 microns. Byproduct adhered to the walls of the pipe during the use of the solution, however the walls washed off clean when 7 liters of water was poured into the top of the column. The flow meter was not working during this test.

TABLE 7

| Time | Flow (m³) | H$_2$S In (ppm) | H$_2$S Out (ppm) | Colour | pH | Fluid Level (in) |
|---|---|---|---|---|---|---|
| 3:30 | 1:475 | 1500-1800 | 0 | dark blue | 10.8 | 45 |
| 3:31 | | " | | | | 97 |
| 3:45 | 1:475 | " | 0 | blue black | | 97 |
| 4:00 | " | " | " | " | | " |
| 4:15 | " | " | " | black | | " |
| 4:30 | " | " | " | " | | " |
| 4:45 | " | " | " | " | | " |
| 5:00 | " | " | " | " | | " |
| 5:15 | " | " | " | black; opaque | | can't see |
| 5:30 | " | " | " | black; opaque | | " |
| 5:45 | " | " | " | black; opaque | | " |
| 6:00 | " | " | " | black; opaque | | " |
| 6:15 | " | " | " | black; opaque | | " |
| 6:30 | " | " | 12 | black; opaque | | " |
| 6:45 | " | " | 100 | | | " |

Test #3

A solution of 5% (v/v) Stabitrol™, 3.5% (w/v) zinc and 50% (v/v) monoethanolamine was tested. The outside temperature was −6° C. and no pressure was applied during the test. The results are shown in Table 8. The solution did not foam during the test. The byproduct of the reaction did not adhere to the walls of the tower, as did the byproduct of the copper solution used in the example above. By 3:45 the byproduct was more grey than black and was getting more viscous. By 4:40, it was very thick and starting to adhere to the walls. The flow meter was not working during this test.

TABLE 8

| Time | Flow (m³) | H$_2$S In (ppm) | H$_2$S Out (ppm) | Colour | pH | Fluid Level (in) |
|---|---|---|---|---|---|---|
| 11:30 | 1:47 | 1800 | 0 | black | 10.1 | 46 |
| 11:45 | " | " | " | " | " | 91 |
| 12:00 | " | " | " | " | " | 92 |
| 12:15 | " | " | " | " | " | 92 |
| 12:30 | " | " | " | " | " | ~94 |
| 12:45 | " | " | " | " | " | " |
| 1:00 | " | " | " | " | " | " |
| 1:15 | " | " | " | " | " | " |
| 1:30 | " | " | " | " | " | " |
| 1:45 | " | " | " | " | " | " |
| 2:00 | " | " | " | " | " | " |
| 2:15 | " | " | " | " | " | " |
| 2:30 | " | " | " | " | " | " |
| 2:45 | " | " | " | " | " | " |
| 3:00 | " | " | " | " | " | " |
| 3:15 | " | " | " | black | " | 91-94 |
| 3:30 | " | " | " | " | " | " |
| 3:45 | " | " | " | grey black | " | " |
| 4:00 | " | " | " | grey | " | " |
| 4:15 | " | " | " | very grey | " | " |
| 4:30 | " | " | 10 | " | " | " |
| 4:40 | " | " | 35 | " | " | " |
| 5:00 | " | " | 120 | " | 8.2 | " |
| | | | | | | 41 |

Test #4

A solution of 5% (v/v) Stabitrol™ and 2.5% (w/v) copper was tested. The outside temperature was 0° C. Results are shown in Table 9. This product turned black when filling. Five minutes after starting the experiment, defoamer had to be added. 17 ml of defoamer in 0.5 L $H_2O$ was added. 25 minutes after the start of the test 6-8" of dark foam was visible on the top of the pipe and by 35 minutes after the start of the test, the fluid reached the top of the tower and there was continued foaming with carry over. The test was stopped because of carry over. While the column was being drained, a sample of the spent fluid was collected, and it immediately started to separate with the clean fluid being blue. This solution does not appear to be able to be used for bubbling gas through to remove $H_2S$ from the gas.

TABLE 9

| Time | Flow ($m^3$) | $H_2S$ In (ppm) | $H_2S$ Out (ppm) | Colour | pH | Fluid Level (in) |
|---|---|---|---|---|---|---|
| 12:05 | | 1500-1800 | | black | | 48 |
| 12:10 | | " | 20 | black | | 9 feet |
| 12:30 | | " | 10 | black | | 45 |
| 12:40 | | " | 10 | black | 1.2 | top of tower |

Test #5

A caustic soda solution (3% (w/v), available from Univar or Strike Oilfield Services) was tested. The outside temperature was 0° C. The results are shown in Table 10. This solution did not foam. Due to an improperly operating flow meter, it is assumed that there was a flow of 3.1 to 3.2 $m^3$ every 15 minutes.

TABLE 10

| Time | Flow ($m^3$) | $H_2S$ In (ppm) | $H_2S$ Out (ppm) | Colour | pH | Fluid Level (in) |
|---|---|---|---|---|---|---|
| 1:32 | | 1800 | | turned black | 11.2 | 474 |
| 1:34 | | " | 0 | " | | 97 |
| 1:37 | | " | 0 | " | | |
| 1:45 | 7.26 | " | 0 | " | | 93 |
| 2:00 | 9.03 | " | 0 | " | | 97 |
| 2:15 | 13.02 | " | 15 | " | | 97 |
| 2:30 | 16.44 | " | 30 | " | | |

Test #6

A solution of 10% (v/v) Stabitrol™ and 9% (w/v) zinc was tested. The outside temperature was 2° C. The results are shown in Table 11. The solution was a light tan color at the beginning of the test. The product did not effectively remove hydrogen sulphide, as the flow rate was too fast and the product could not react with the $H_2S$.

TABLE 11

| Time | Flow ($m^3$) | $H_2S$ In (ppm) | $H_2S$ Out (ppm) | Colour | pH | Fluid Level (in) |
|---|---|---|---|---|---|---|
| 3:10 | 16.83 | 1800 | | turned black | 1.3 | 48 |
| 3:11 | | | | | | 97 |
| 3:15 | 17.90 | " | 1800 | " | | 97 |

Test #7

A solution of 5% (v/v) Stabitrol™ and 50% (v/v) monoethanolamine was tested. The outside temperature was −3° C. The results are shown in Table 12. The solution was gold-colored at the beginning. Bubble action was visible when the control valve was fully opened. There was no foaming. 30 minutes after the start of the test, the fluid was much darker. The byproduct of this reaction smelled like $H_2S$. Black flakes were produced during the test and the composition of these flakes is unknown.

TABLE 12

| Time | Flow ($m^3$) | $H_2S$ In (ppm) | $H_2S$ Out (ppm) | Colour | pH | Fluid Level (in) |
|---|---|---|---|---|---|---|
| 10:30 | 19.06 | 2000 | 0 | black | 10.3 | 49 |
| 10:30 | | | | | | 89 |
| 10:45 | 22.56 | " | 0 | dark | | " |
| 11:00 | 26.08 | " | 15 | black | | 99 |
| 11:15 | 29.54 | " | 120 | black | 9.3 | " |

Test #8

A solution of 100% (v/v) monoethanolamine was tested. The outside temperature was −2° C. The results are shown in Table 13. The solution was very difficult to drain out of the tower after this test was completed—although it was very runny, something held the flow back.

TABLE 13

| Time | Flow ($m^3$) | $H_2S$ In (ppm) | $H_2S$ Out (ppm) | Colour | pH | Fluid Level (in) |
|---|---|---|---|---|---|---|
| 11:55 | 29.97 | 2000 | 0 | dark | 12.5 | 55 |
| | 33.28 | " | 5 | dark | | 103 |
| 12:25 | 36.64 | " | 20 | dark | | " |

Test #9

A solution of 5% (v/v) Stabitrol™, 3.5% (w/v) zinc and 50% (v/v) monoethanolamine was tested. The outside temperature was 0° C. The results are shown in Table 14. By 4:00 the solution was still very fluid and was not sticking to the walls of the tower. By 6:30 the fluid was getting stickier, by 7:10 it was sticking to pipe walls. The ending $H_2S$ was 2,000 ppm.

TABLE 14

| Time | Flow ($m^3$) | $H_2S$ In (ppm) | $H_2S$ Out (ppm) | Colour | pH | Fluid Level (in) |
|---|---|---|---|---|---|---|
| 1:07 | 37.61 | 2000 | 0 | dark | 10.1 | 47 |
| 1:07 | | | | | | 86 |
| 1:15 | 40.10 | " | " | dark | | " |
| 1:30 | 43.37 | " | " | " | | " |
| 1:45 | 47.06 | " | " | " | | " |
| 2:00 | 50.48 | " | " | " | | " |
| 2:07 | 52.05 | " | " | " | | " |
| 2:15 | 53082 | " | " | " | | " |
| 2:30 | 57.13 | " | " | " | | " |
| 2:45 | 60.47 | " | " | " | | " |
| 3:00 | 63.77 | " | " | " | | " |
| 3:15 | 67.07 | " | " | " | | " |
| 3:30 | 70.52 | " | " | " | | " |
| 3:45 | 73.94 | " | " | " | | " |
| 4:00 | 77.43 | " | " | " | | " |

TABLE 14-continued

| Time | Flow (m³) | H₂S In (ppm) | H₂S Out (ppm) | Colour | pH | Fluid Level (in) |
|---|---|---|---|---|---|---|
| 4:15 | 80.86 | 2000 | 0 | black | | 84 |
| 4:30 | 84.16 | " | " | " | | " |
| 4:45 | 87.36 | " | " | | | " |
| 5:00 | 91.06 | " | " | " | | " |
| 5:15 | 94.46 | " | " | " | | " |
| 5:30 | 97.83 | " | " | " | | 80 |
| 5:45 | 101.36 | " | " | " | | " |
| 6:00 | 105.05 | " | " | " | | " |
| 6:15 | 108.62 | " | " | " | | 82 |
| 6:30 | 112.17 | " | " | " | | " |
| 6:45 | 115.73 | " | " | " | | " |
| 7:00 | 119.06 | " | 22 | grey black | | " |
| 7:10 | 121.38 | " | 60 | " | | " |
| 7:15 | 122.33 | " | 80 | " | | " |
| 7:25 | 124.61 | " | 40 | " | | " |
| 7:30 | 125.77 | " | 60 | " | | " |
| 7:45 | 129.15 | " | 120 | " | | " |

Test #10

A solution of 2.5% (v/v) Stabitrol™; 1.75% (w/v) zinc and 25% (v/v) monoethanolamine was tested. The outside temperature was 3° C. The results are shown in Table 15. At 4:15 the solution was very watery. The end byproduct was very watery, but grey in colour. This may be significant when it applies to a packed column or packed vessel using reverse circulation, as the byproduct will circulate well, and will not be difficult to clean out of a vessel. The test was shut down at 5 pm.

TABLE 15

| Time | Flow (m³) | H₂S In (ppm) | H₂S Out (ppm) | Colour | pH | Fluid Level (in) |
|---|---|---|---|---|---|---|
| 12:55 | 130.53 | 2000 | 0 | black | 10.4 | 41 |
| 1:15 | 135.04 | " | " | " | | 76 |
| 1:30 | 138.58 | " | " | " | | " |
| 1:45 | 141.52 | " | " | " | | " |
| 2:00 | 144.94 | " | " | " | | " |
| 2:15 | 148.45 | " | " | " | | " |
| 2:30 | 151.92 | " | " | black/grey | | " |
| 2:45 | 154.84 | " | " | " | | " |
| 3:00 | 158.21 | " | " | " | | " |
| 3:15 | 161.35 | " | " | " | | " |
| 3:30 | 164.28 | " | " | " | | " |
| 3:45 | 166.90 | " | " | " | | " |
| 4:00 | 169.70 | " | " | " | | " |
| 4:15 | 172.60 | " | 5 | " | 8.4 | " |

Test #11

A solution of Sulfa Scrub HSW2001 (Baker Petrolite) was tested. The outside temperature was −4° C. The results are shown in Table 16. This solution did not foam and was still very fluid at 3:45. This solution contains 10% formaldehyde. After breakthrough occurs, the solution appears to maintain relatively low emission of H₂S for some time, but these emissions would be unacceptable in applications where 0 ppm must be maintained.

TABLE 16

| Time | Flow (m³) | H₂S In (ppm) | H₂S Out (ppm) | Colour | pH | Fluid Level (in) |
|---|---|---|---|---|---|---|
| 11:50 | 173.21 | 400 | 0 | black | | 42 |
| 12:15 | 179.23 | " | " | " | | 76 |
| 12:30 | 182.77 | " | " | " | | " |
| 12:45 | 186.49 | " | " | " | | " |
| 1:00 | 190.10 | " | " | " | | " |
| 1:15 | 193.53 | " | " | " | | " |
| 1:30 | 196.90 | " | " | " | | " |
| 1:45 | 200.26 | " | " | " | | " |
| 2:00 | 203.52 | " | " | " | | " |
| 2:15 | 206.85 | " | " | " | | " |
| 2:30 | 209.90 | " | " | " | | 66 |
| 2:45 | 213.08 | " | " | " | | " |
| 3:00 | 216.34 | " | " | " | | " |
| 3:15 | 219.60 | " | " | " | | 61 |
| 3:30 | 222.77 | " | " | " | | " |
| 3:45 | 226.14 | " | " | " | | " |
| 4:00 | 229.49 | 400 | 0 | black | | 61 |
| 4:15 | 232.94 | " | " | " | | " |
| 4:30 | 236.23 | " | " | " | | " |
| 4:45 | 239.64 | " | " | " | | " |
| 5:00 | 243.22 | " | " | " | | " |
| 5:15 | 247.18 | " | " | " | | " |
| 5:30 | 250.70 | " | " | " | | " |
| 5:45 | 254.36 | " | " | " | | " |
| 6:00 | 258.20 | " | " | " | | " |
| 6:15 | 261.46 | " | 5 | " | | " |
| 6:30 | 264.80 | " | 10 | " | | 60 |
| 6:45 | 267.86 | " | 10 | " | | " |
| 7:00 | 271.05 | " | 15 | " | | " |
| 7:15 | 274.35 | " | 20 | " | | " |
| 7:30 | 277.42 | " | 15 | " | | " |
| 7:45 | 280.79 | 200 | 25 | " | 8.2 | " |

Test #12

A solution of HSW0705F (Baker Petrolite) was tested. The outside temperature was −12° C. and 28 psi of pressure was applied to the solution. The results are shown in Table 17. No foaming occurred. At the end of the test there was 200 ppm H₂S In. Gas volume dropped off dramatically.

TABLE 17

| Time | Flow (m³) | H₂S In (ppm) | H₂S Out (ppm) | Colour | pH | Fluid Level (in) |
|---|---|---|---|---|---|---|
| 9:55 | 290.00 | 400 | 0 | clear | 10.4 | 42 |
| 10:15 | 294.44 | " | " | " | | 72 |
| 10:30 | 297.84 | " | 10 | fairly clear | " | " |
| 10:45 | 300.23 | " | 15 | " | " | 62 |
| 11:00 | 302.15 | " | " | " | " | " |
| 11:15 | 303.70 | " | 10 | " | " | " |

Test #13

A solution of Sulfa Scrub HSW2001 (Baker Petrolite) was tested. The outside temperature was −12° C. The results are shown in Table 18. At 2:00 the test had to be shut down in order to install another valve for sampling raw gas. The solution did not foam. At 4:30 the test was shut down as there were problems with flow rate.

TABLE 18

| Time | Flow (m³) | H₂S In (ppm) | H₂S Out (ppm) | Colour | pH | Fluid Level (in) |
|---|---|---|---|---|---|---|
| 11:45 | 303.95 | 2000 | 0 | clear, dark | 9.7 | 42 |
| 12:00 | 305.06 | " | " | " | " | 53 |
| 12:15 | 306.15 | " | " | " | " | " |
| 12:30 | 307.25 | " | " | " | " | " |
| 12:45 | 308.35 | " | " | " | " | " |
| 1:00 | 309.35 | " | " | " | " | " |
| 1:15 | | " | " | " | " | " |
| 1:30 | 310.53 | " | " | " | " | " |
| 2:00 | 311.17 | " | " | " | " | " |
| | | " | " | " | " | " |
| 2:30 | 311.72 | <100 ppm | " | " | " | " |
| 3:00 | 312.79 | " | " | " | " | " |
| 3:30 | 314.52 | 500 ppm | " | " | " | " |
| 4:30 | 314.52 | | | | | |

Test #14

A solution of Sulfa Scrub HSW2001 (Baker Petrolite) was tested. The outside temperature was −12° C. The results are shown in Table 19. This is a continuation of the test shown in Table 18, which had to be shut down because the gas volume was only 11 m³ and the concentration of H₂S dropped to less than 100 ppm. The fluid was left in the test tower and used in this test, which occurred two days later. When the test was stopped at 5:20 there was an extraordinarily offensive smell emitting from it. As with the other test (test #11) of this solution, the results of which are shown in Table 16, after breakthrough the solution is able to maintain 10 ppm to 20 ppm H₂S for a long period of time.

TABLE 19

| Time | Flow (m³) | H₂S In (ppm) | H₂S Out (ppm) | Colour | pH | Fluid Level (in) |
|---|---|---|---|---|---|---|
| 10:55 | 314.76 | 400 | 0 | clear, dark | — | 40 |
| 11:30 | 322.50 | 400 | 0 | " | — | 71 |
| 12:00 | 330.40 | 400 | 0 | " | — | " |
| 12:30 | 338.09 | 400 | 0 | " | — | " |
| 1:00 | 345.30 | 300 | 0 | " | — | 66 |
| 1:30 | 351.50 | 300 | 0 | " | — | " |
| 2:00 | 358.33 | 500 | 10 | " | — | " |
| 2:30 | 364.92 | " | " | " | — | " |
| 3:00 | 371.60 | 350 | " | " | — | 62 |
| 3:30 | 377.64 | " | 15 | " | — | " |
| 4:00 | 384.80 | " | " | " | — | " |
| 4:30 | 392.22 | 100-200 | 10 | " | — | " |
| 5:00 | 460.07 | 200 | 15 | " | — | " |
| 5:20 | 405.08 | 200 | 20 | " | 8.1 | 35 |

Test #15

A solution of 30% (w/v) of ammonium hydroxide (Strike Oilfield Services, or, Univar) was tested using the above methods. The outside temperature was −7° C. The results are shown in Table 20. By 7:15 the solution was very dark.

TABLE 20

| Time | Flow (m³) | H₂S In (ppm) | H₂S Out (ppm) | Colour | pH | Fluid Level (in) |
|---|---|---|---|---|---|---|
| 5:50 | 405.23 | 200 | 0 | milky, clear | 14.4 | 44 |
| 5:53 | 405.70 | " | " | grey, dark | " | 85 |
| 6:00 | 407.96 | " | " | dark | " | 97 |
| 6:15 | 410.98 | 500 | " | " | " | 79 |
| 6:30 | 414.47 | " | " | " | " | " |

TABLE 20-continued

| Time | Flow (m³) | H₂S In (ppm) | H₂S Out (ppm) | Colour | pH | Fluid Level (in) |
|---|---|---|---|---|---|---|
| 6:45 | 418.00 | " | " | " | " | " |
| 7:00 | 421.64 | " | 10 | " | " | " |
| 7:15 | 425.48 | " | 35 | " | " | " |
| 7:30 | 428.72 | " | 250 | " | 9.8 | 38 |

Test #16

A solution of 1% (v/v) sulphuric acid, 3.5% (w/v) zinc and 50% (v/v) monoethanolamine was tested. The outside temperature was 12° C. and no pressure was applied to the solution. The results are shown in Table 21. This solution did not foam. By 3:30 the fluid was so dark that it was not possible to see inside the pipe. By 5:30 it was very thick and black.

TABLE 21

| Time | Flow (m³) | H₂S In (ppm) | H₂S Out (ppm) | Colour | pH | Fluid Level (in) |
|---|---|---|---|---|---|---|
| 10:40 | 430.17 | 400 | 0 | olive | | 43 |
| 11:00 | 434.01 | " | " | " | | 76 |
| 11:30 | 440.30 | " | " | " | | " |
| 12:00 | 446.32 | " | " | " | | " |
| 12:30 | 451.74 | " | " | " | | " |
| 1:00 | 456.51 | " | " | " | | " |
| 1:30 | 460.45 | " | " | " | | " |
| 2:00 | 464.80 | " | " | " | | " |
| 2:30 | 467.60 | " | " | " | | " |
| 3:00 | 469.59 | " | " | " | | " |
| 3:30 | 471.06 | 1000 | " | " | | " |
| 4:00 | 472.47 | " | " | " | | " |
| 4:30 | 473.56 | " | " | " | | " |
| 5:00 | 474.80 | 2000 | 10 | dark | | " |
| 5:15 | 475.44 | " | 60 | " | | " |
| 5:30 | 476.22 | " | 85 | " | | 38 |

Test #17

A solution of 5% (v/v) Stabitrol™, 3.5% (w/v) zinc and 50% (v/v) monoethanolamine was tested. The outside temperature was 23° C. and there was 5 psi of pressure in the tower. The results are shown in Table 22. At 13:19 the flow was increased and pressure adjusted to 7 psi. The solution was still light and foamy at 13:45. The test was shut down at 14:15 because of an H₂S monitor alarm. At 8:30 the next day the test was continued. The solution was so dark at that time that it wasn't possible to see into the tube.

TABLE 22

| Time | Flow (m³) | H₂S In (ppm) | H₂S Out (ppm) | Colour | Pressure (psi) | Fluid Level (in) |
|---|---|---|---|---|---|---|
| 11:19 | 534.35 | 1500 | 0 | dark brown | 5 | 49 |
| 12:10 | 542.40 | " | " | " | 5 | 90 |
| 12:19 | 544.00 | " | " | " | 5 | " |
| 13:19 | 554.00 | " | " | " | 9 | " |
| 13:45 | 559.00 | " | " | light | " | " |
| 14:15 | 563.96 | " | " | " | " | " |
| 8:30 | 563.96 | 2000 | " | " | 5 | " |
| 9:00 | 568.04 | " | " | brown | 8 | " |
| 9:30 | 572.26 | " | " | " | 8 | " |
| 10:00 | 576.83 | " | " | " | 7 | " |
| 10:15 | 578.40 | " | " | " | 7 | " |
| 10:30 | 581.05 | " | 20 | " | 7 | " |

Test #18

A solution of 5% (v/v) Stabitrol™, 4.5% (w/v) zinc and 50% (v/v) monoethanolamine was tested. The outside temperature was not recorded and there was no pressure in the column, The results are shown in Table 23. There was some difficulty, in this test, with the $H_2S$ readings. This solution did generate foam. Then end value for $H_2S$ In was determined by gas tube RAE. (**)

TABLE 23

| Time | Flow ($m^3$) | $H_2S$ In (ppm) | $H_2S$ Out (ppm) | Colour | pH | Fluid Level (in) |
|---|---|---|---|---|---|---|
| 10:14 | 484.36 | | 0 | brown | | 46 |
| 10:30 | 486.66 | | 0 | " | | 75 |
| 11:05 | | | 0 | " | | |
| 11:14 | 493.60 | | 0 | " | | |
| 11:37 | | | 0 | " | | 84 |
| 12:14 | | | 0 | light brown | | 96 |
| 12:15 | 502.13 | | 0 | " | | |
| 13:12 | 510.00 | | 0 | " | | 96 |
| 14:15 | 517.07 | | 0 | opaque | | |
| 15:17 | 523.87 | | 0 | | | |
| 16:15 | 526.51 | 1500 ** | 14 | | | 69 |
| | | | ambient @ 16:10 | | | |

Test #19

A solution of 5% (v/v) Stabitrol™, 4.5% (w/v) zinc and 50% (v/v) diglycolamine was tested. The outside temperature was 24° C. and there was 3 psi of pressure within the tower or column. The results are shown in Table 24. A layer of foam developed immediately, and at 11:15, 1 liter of foam was pulled off the top of the liquid. By 11:30, foaming and carry over had stopped. A sample of gas was taken at 15:15, and $H_2S$ reading was at 0 ppm. At this time the solution was very fluid.

TABLE 24

| Time | Flow ($m^3$) | $H_2S$ In (ppm) | $H_2S$ Out (ppm) | Colour | pH | Fluid Level (in) |
|---|---|---|---|---|---|---|
| 11:10 | 581.07 | 1500+ | 0 | | | 47 |
| 11:15 | | " | 0 | | | |
| 11:30 | 583.90 | " | 0 | | | |
| 12:00 | 588.36 | " | 0 | | | 72 |
| 12:25 | 592.11 | " | 40 | | | 31 |

Test #20

A solution of 2.5% (v/v) Stabitrol™, 1.75% (w/v) zinc and 50% (v/v) monoethanolamine was tested. The outside temperature was 26° C. and 5 psi of pressure existed within the tower. The results are shown in Table 25. By 13:00 the byproduct began to stick to the sides of the tower. After the test was over, the solution drained very well as a very liquid fluid.

TABLE 25

| Time | Flow ($m^3$) | $H_2S$ In (ppm) | $H_2S$ Out (ppm) | Colour | Pressure (psi) | Fluid Level (in) |
|---|---|---|---|---|---|---|
| 11:30 | 592.23 | 2000+ | 0 | brown | 5 | 46 |
| 12:00 | 597.94 | " | 0 | " | 5 | 92 |
| 12:30 | 603.51 | " | 0 | " | 5 | " |

TABLE 25-continued

| Time | Flow ($m^3$) | $H_2S$ In (ppm) | $H_2S$ Out (ppm) | Colour | Pressure (psi) | Fluid Level (in) |
|---|---|---|---|---|---|---|
| 13:00 | 609.45 | " | 0 | " | 5 | " |
| 13:30 | 615.08 | " | 0 | darker | 5 | " |
| 13:45 | 617.91 | " | 20 | very dark | 5 | " |

Test #21

A solution of 3.5% (w/v) zinc and 25% (v/v) monoethanolamine was tested. The outside temperature was 26° C. and 5 psi of pressure was applied to the solution. The results are shown in Table 26. The solution was fairly thick to begin with. At 3:00 the flow was cut, because the pressure was too high, after which the pressure was held at 5 psi.

TABLE 26

| Time | Flow ($m^3$) | $H_2S$ In (ppm) | $H_2S$ Out (ppm) | Colour | Pressure (psi) | Fluid Level (in) |
|---|---|---|---|---|---|---|
| 2:15 | 617.92 | 2000+ | 0 | brown | 5 | 46 |
| 3:00 | 627.20 | " | " | " | 10 | 102 |
| 3:15 | 629.96 | " | " | " | 5 | " |
| 3:45 | 635.90 | " | " | " | 5 | 97 |
| 4:15 | 641.02 | " | " | " | 5 | 92 |
| 4:45 | 647.21 | " | " | " | 5 | " |
| 5:15 | 653.28 | " | " | " | 5 | 97 |
| 5:45 | 659.00 | " | " | " | 5 | " |
| 6:15 | 664.57 | " | " | " | 5 | 92 |
| 6:45 | 669.97 | " | 10 | " | 5 | |

Test #22

A solution of 3.6% (w/v) zinc and 20% (v/v) monoethanolamine was tested. The outside temperature was 24° C. and 5 psi of pressure existed within the tower or column. The results are shown in Table 27. In this solution the zinc did not seem to be completely dissolved.

Sticking of byproduct to the sides of the vessel was observed beginning at 12:40. The fluid was thin and drained well from the tower after the test was over.

TABLE 27

| Time | Flow ($m^3$) | $H_2S$ In (ppm) | $H_2S$ Out (ppm) | Colour | Pressure (psi) | Fluid Level (in) |
|---|---|---|---|---|---|---|
| 11:20 | 670.00 | 2000 | 0 | white | 5 | 46 |
| 12:40 | 683.75 | " | " | yellow brown | 5 | 92 |
| 1:20 | 691.90 | " | " | " | 5 | " |
| 2:20 | 704.58 | " | " | " | 5 | " |
| 2:50 | 710.43 | " | " | " | 5 | " |
| 3:20 | 716.77 | " | " | " | 5 | " |
| 3:50 | 721.53 | " | " | " | 5 | " |
| 4:25 | 727.75 | " | 15 | red grey | 5 | " |

Test #23

Nine liters of drilling mud was mixed with 300 ml of a solution of 5% Stabitrol™, 3.5% zinc and 50% monoethanolamine, and 700 ml of water. The outside temperature was 24° C. and no pressure was applied to the solution. The results are shown in Table 28. Flow was low in this test.

TABLE 28

| Time | Flow ($m^3$) | $H_2S$ In (ppm) | $H_2S$ Out (ppm) | Colour | pH | Fluid Level (in) |
|---|---|---|---|---|---|---|
| 3:30 | 727.75 | 2000+ | 0 | brown | | 46 |
| 3:45 | 728.07 | " | " | " | | 72 |
| 4:00 | 728.30 | " | 4 | " | | " |
| 4:15 | 728.85 | " | 500 | " | | " |
| | | | | | | 46 |

Test #24

A solution of 5% (v/v) Stabitrol™, 3.5% (w/v) zinc and 50% (v/v) monoethanolamine, was tested. In this test the monoethanolamine used was new, rather than recycled monoethanolamine. The outside temperature was 20° C. and 5 psi of pressure was applied to the solution. The results are shown in Table 29. By 5:30, some byproduct began to stick to the sides of the vessel. There did not appear to be any noticeable difference in the performance of this solution as compared to the previous tests which used recycled monoethanolamine.

The spent fluid was left in the tower overnight. The next morning, approximately 3.5 liters of thick, grey spent product was added to 4 liters of water, and sour gas flow was started. The meter reading ($H_2S$ Out) at 9:40 am with a flow of 775.67 $m^3$, was 0 ppm. At 10:00 am with a flow of 777.47 $m^3$ the reading was 15 ppm.

TABLE 29

| Time | Flow ($m^3$) | $H_2S$ In (ppm) | $H_2S$ Out (ppm) | Colour | Pressure (psi) | Fluid Level (in) |
|---|---|---|---|---|---|---|
| 1:00 | 728.58 | 2000+ | 0 | dark | 5 | 46 |
| 1:30 | 734.12 | " | 0 | " | 8 | 78 |
| 2:00 | 739.64 | " | 0 | " | 8 | " |
| 2:30 | 744.92 | " | 0 | getting darker | 10 | " |
| 3:00 | 749.79 | " | 0 | " | 8 | " |
| 3:30 | 754.52 | " | 0 | " | 3 | " |
| 4:00 | 579.70 | " | 0 | " | 5 | " |
| 4:30 | 764.92 | " | 0 | " | 5 | " |
| 5:00 | 770.09 | " | 0 | " | 9 | " |
| 5:30 | 775.09 | " | 100 | looks darker | 6 | " |

Test #25

A solution of 5% (v/v) Stabitrol™, 3.5% (w/v) zinc and 37.5% (v/v) monoethanolamine, was tested. The outside temperature was 24° C. and 15 psi of pressure was applied to the solution initially, but it was cut back to 5 psi. The results are shown in Table 30. By 2 pm the byproduct was starting to stick to the sides of the tower. The fluid was runny and easy to drain from the tower after the test was over.

TABLE 30

| Time | Flow ($m^3$) | $H_2S$ In (ppm) | $H_2S$ Out (ppm) | Colour | Pressure (psi) | Fluid Level (in) |
|---|---|---|---|---|---|---|
| 10:22 | 777.60 | 2000 | 0 | olive | 5 | 45 |
| 10:30 | 778.50 | " | 0 | " | 8 | 92 |
| 11:00 | 781.00 | " | 0 | " | 9 | 98 |
| 11:30 | 783.44 | " | 0 | " | 10 | 82 |
| 12:00 | 787.41 | " | 0 | " | 10 | " |
| 12:30 | 790.88 | " | 0 | " | 10 | " |
| 1:00 | 795.01 | " | 0 | " | 10 | " |
| 1:30 | 799.32 | " | 0 | " | 10 | " |
| 2:00 | 804.62 | " | 0 | " | 10 | " |
| 2:30 | 809.95 | " | 0 | getting darker | 10 | " |
| 3:00 | 814.85 | " | 60 | dark | 10 | " |

Summary of Tests

Table 31 compares the results obtained with some of the solutions tested above. These results are adjusted to an $H_2S$ In of 2,000 ppm, a constant pressure and a constant flow of gas.

TABLE 31

| Solution Tested (10 litres) | Elapsed Time Before Breakthrough of $H_2S$ (minutes) | Sour Gas Scrubbed Before Breakthrough of $H_2S$ ($m^3$) |
|---|---|---|
| 5% (v/v) Stabitrol ™; 3.5% (w/v) zinc; 50% (v/v) monoethanolamine | 353 | 81.45 |
| Caustic Soda | 39 | 8.25 |
| Ammonia | 18 | 4.10 |
| Sulfa Scrub HSW2001 | 77 | 17.65 |
| HSW0705F | 7 | 2.04 |

When allowing for pressure differentials, $H_2S$ variances and temperature it is calculated that one liter of the 5% Stabitrol™, 3.5% zinc, 50% monoethanolamine solution disclosed herein will neutralize 8 to 9 cubic meters of gas comprising $H_2S$ at 2,000 ppm.

Diglycolamine (DGA) and MDEA were tested as alternative amines to monoethanolamine, and although they work to some degree, neither of them work as well as monoethanolamine for scavenging $H_2S$ when used in the solution of this invention.

Example 4

The corrosiveness of a 5% (v/v) Stabitrol™; 3.5% (w/v) zinc; 50% (v/v) monoethanolamine solution was tested using a wheel test method (NACE Procedure 1D182). The wheel test is the dynamic test performed by placing the test fluid in a 1250 gm (150-cc) bomb bottle with a metal coupon. The bottles are pressurized with sour gas if any sour test is to be conducted with pressure in the system, and capping the bottle. The bottle is then agitated for a period of time by securing it in the circumference of a wheel and rotating it under pressure and temperature. The test is normally run for 2 to 3 weeks. After the test is completed, the tested coupons are removed from the bomb bottle and the pitting tendency is evaluated.

Two (2) pieces of 7.65 cm×1.125 cm×1.06 mm shim stock SAE 1020 steel were used as a Coupon. This material can be readily observed for pitting tendency. A small hole of (5-mm in diameter) was drilled at one end of the coupons in order to place in the plastic cap. Coupons were cleaned with benzene, wiped dry with a clean cloth and stored before weighing, and fingerprints were avoided by handling with clean latex gloves and forceps. The initial weight of the coupons was measured.

A stainless steel bomb bottle (150 cc capacity, high pressure and temperature) was cleaned with toluene followed by isopropanol solution, blow dried with air and kept sealed before using. Then the coupon was placed in the plastic cap at the one end of the bomb. The bottle was evacuated to avoid any air contamination. 100 cc of the solution being tested was drawn into the test bomb bottle to fill approximately ⅔ of its capacity. The capped bombs were placed on holders on the wheel and rotated at 20° C. for 2 weeks.

After this time, the coupons were retrieved from the bomb bottle, rinsed with xylene to remove solution film, wiped with steel wool pad to remove any corrosion by-product, and weighed. Then, the coupons were placed in a plastic bag and photographed.

This procedure may have many variables such as the effect of various contaminants in the solution, as well as air contamination. The weight loss for each coupon was determined and duplicates averaged and percent corrosion is calculated as follows:

% Corrosion=Weight loss (mg)/Weight before (mg)×100.

The results obtained for the 5% Stabitrol™; 3% zinc; 50% monoethanolamine solution are recorded in Table 32, and indicate that the solution is not corrosive.

TABLE 32

| ID | Initial Weight, (g) | Final Weight (g) | % Corrosion |
|---|---|---|---|
| 1 | 5.751 | 5.751 | 0.0 |
| 2 | 5.801 | 5.801 | 0.0 |
| 3 | 5.809 | 5.809 | 0.0 |
| 4 (Blank) | 6.004 | 6.004 | 0.0 |
| | | Average Corrosion | 0.0 |

Example 5

Samples of sour gas that were untreated or treated with a test solution, according to the methods disclosed in Example 3 above, were collected. These samples were subjected to gas analysis and trace sulphur analysis to determine which types of sulphur compounds were removed from the sample by treatment with the solution. The results of the tests are outlined in tables below. For each sulphur compound tested, the method detection limit was 0.1 ppm. These results indicate that the solution of this invention consistently reduces carbonyl sulphide, methyl mercaptan, ethyl mercaptan and iso-butyl mercaptan. The solution also scavenges carbon dioxide in colder temperatures.

Gas samples collected before and after the use of a solution of 5% Stabitrol™ (v/v), 3.5% Zinc (w/v), and 50% (v/v) monoethanolamine were analysed. The results in Table 33 indicate that the solution tested reduces, in addition to $H_2S$, carbonyl sulphide, methyl mercaptan, ethyl mercaptan, n-propyl mercaptan, iso-butyl mercaptan and carbon dioxide. These results indicate that the solution of this invention will remove many mercaptans from a gas.

TABLE 33

| Sulphur Compound | [ ] in gas before treatment (ppm) | [ ] in treated sample (ppm) [sampled at 11:30] | [ ] in treated sample (ppm) [sampled at 12:00] |
|---|---|---|---|
| hydrogen sulphide | 1240 | <0.1 | <0.1 |
| carbonyl sulphide | 2.0 | 0.2 | 0.2 |
| methyl mercaptan | 3.1 | 0.1 | 0.3 |
| ethyl mercaptan | 5.5 | 0.4 | 1.4 |
| dimethyl disulphide | <0.1 | <0.1 | 0.1 |

TABLE 33-continued

| | | | |
|---|---|---|---|
| carbon disulphide | <0.1 | <0.1 | <0.1 |
| iso-propyl mercaptan | 2.1 | 1.1 | 4.7 |
| tert-butyl mercaptan | 0.1 | 0.2 | 0.2 |
| n-propyl mercaptan | 0.9 | 0.1 | 0.3 |
| methyl ethyl sulphide | <0.1 | 0.2 | 0.1 |
| sec-butyl mercaptan | 1.3 | 0.4 | 1.0 |
| thiophene | <0.1 | <0.1 | <0.1 |
| iso-butyl mercaptan | 8.0 | <0.1 | <0.1 |
| n-butyl mercaptan | <0.1 | <0.1 | <0.1 |
| tert-butyl methyl sulphide | <0.1 | <0.1 | <0.1 |
| dimethyl sulphide | <0.1 | <0.1 | <0.1 |
| diethyl sulphide | <0.1 | <0.1 | <0.1 |
| unidentified sulphur components | 7.7 | 48.5 | 5.1 |
| total organic sulphur | 1270 | 52.8 | 13.4 |

| Other | Mole Frac. | Mole Frac. | Mole Frac. |
|---|---|---|---|
| $H_2$ | trace | 0.0000 | 0.0000 |
| He | 0.0001 | 0.0001 | 0.0001 |
| $N_2$ | 0.0010 | 0.0036 | 0.0002 |
| $CO_2$ | 0.0420 | 0.0147 | 0.0209 |
| $H_2S$ | 0.0012 | 0.0000 | 0.0000 |

Gas samples collected before and after the use of a solution of 5% Stabitrol™, 3.5% zinc and 37.5% monoethanolamine, were tested. The result of the on site test for this solution was reported in table 30, above. The sour gas sample was taken at 11:30 and treated gas samples were taken at 11:30 (column 1), 12:30 (column 2) and 14:30 (column 3). The samples were analysed for mole fraction of various compounds (see bottom of table), and some of the samples were subjected to a trace sulphur analysis. The results in Table 34 indicate that the solution tested reduces, in addition to $H_2S$, carbonyl sulphide, methyl mercaptan and ethyl mercaptan. These results indicate that the solution of this invention will remove many mercaptans from a gas.

TABLE 34

| Sulphur Compound | [ ] in sour gas (ppm) | [ ] in treated gas sample (ppm) | | |
|---|---|---|---|---|
| | | 1 | 2 | 3 |
| hydrogen sulphide | 1200 | <0.1 | | 0.8 |
| carbonyl sulphide | 1.9 | 0.2 | | <0.1 |
| methyl mercaptan | 3.2 | 0.4 | | 1.4 |
| ethyl mercaptan | 4.3 | 1.2 | | 3.8 |
| dimethyl disulphide | <0.1 | <0.1 | | <0.1 |
| carbon disulphide | 0.2 | <0.1 | | 0.2 |
| iso-propyl mercaptan | 3.2 | 2.5 | | 5.5 |
| tert-butyl mercaptan | <0.1 | 0.1 | | 0.1 |
| n-propyl mercaptan | 0.8 | 0.4 | | 0.9 |
| methyl ethyl sulphide | <0.1 | <0.1 | | <0.1 |
| sec-butyl mercaptan | 0.7 | 0.7 | | 1.1 |
| thiophene | <0.1 | <0.1 | | <0.1 |
| iso-butyl mercaptan | <0.1 | <0.1 | | <0.1 |
| n-butyl mercaptan | <0.1 | <0.1 | | <0.1 |
| tert-butyl methyl sulphide | <0.1 | <0.1 | | <0.1 |
| dimethyl sulphide | <0.1 | <0.1 | | <0.1 |
| diethyl sulphide | <0.1 | <0.1 | | <0.1 |
| unidentified sulphur components | <0.1 | <0.1 | | <0.1 |

TABLE 34-continued

| total organic sulphur | 1210 | 5.5 | 13.8 | |
|---|---|---|---|---|
| Other | Mole Frac. | Mole Frac. | Mole Frac. | Mole Frac. |
| $H_2$ | 0.0000 | trace | trace | 0.0000 |
| He | 0.0000 | 0.0001 | 0.0001 | 0.0001 |
| $N_2$ | 0.0046 | 0.0008 | 0.0040 | 0.0010 |
| $CO_2$ | 0.0365 | 0.0416 | 0.0385 | 0.0405 |
| $H_2S$ | 0.0012 | 0.0000 | 0.0000 | Trace |

Gas samples collected before and after the use of a solution of 5% Stabitrol™, 3.5% zinc and 50% monoethanolamine, were tested. The result of the on site test for this solution was reported in Table 29, above. The sour gas sample was taken at 12:40 and treated gas samples were taken at 14:00 (column 1), 15:00 (column 2), 16:00 (column 3) and 17:00 (column 4). The samples were analysed for mole fraction of various compounds (see bottom of table), and some of the samples were subjected to a trace sulphur analysis. The results in Table 35 indicate that the solution tested reduces, in addition to $H_2S$, carbonyl sulphide, methyl mercaptan and ethyl mercaptan. These results indicate that the solution of this invention will remove many mercaptans from a gas.

TABLE 35

| | [ ] in sour gas | [ ] in treated gas sample (ppm) | | | |
|---|---|---|---|---|---|
| Sulphur Compound | (ppm) | 1 | 2 | 3 | 4 |
| hydrogen sulphide | 1240 | <0.1 | | | 0.4 |
| carbonyl sulphide | 0.9 | <0.1 | | | <0.1 |
| methyl mercaptan | 3.1 | 0.8 | | | 1.2 |
| ethyl mercaptan | 4.6 | 2.4 | | | 3.9 |
| dimethyl disulphide | <0.1 | <0.1 | | | <0.1 |
| carbon disulphide | <0.1 | 0.8 | | | 0.4 |
| iso-propyl mercaptan | 3.7 | 3.3 | | | 4.0 |
| tert-butyl mercaptan | <0.1 | 0.2 | | | 0.1 |
| n-propyl mercaptan | 0.8 | 0.6 | | | 0.9 |
| methyl ethyl sulphide | <0.1 | <0.1 | | | <0.1 |
| sec-butyl mercaptan | 1.3 | 1.0 | | | 0.9 |
| thiophene | <0.1 | <0.1 | | | <0.1 |
| iso-butyl mercaptan | <0.1 | <0.1 | | | <0.1 |
| n-butyl mercaptan | <0.1 | <0.1 | | | <0.1 |
| tert-butyl methyl sulphide | <0.1 | <0.1 | | | <0.1 |
| dimethyl sulphide | <0.1 | <0.1 | | | <0.1 |
| diethyl sulphide | <0.1 | <0.1 | | | <0.1 |
| unidentified sulphur components | <0.1 | <0.1 | | | <0.1 |
| total organic sulphur | 1270 | 9.1 | | | 11.8 |
| Other | Mole Frac. | Mole Frac. | Mole Frac. | Mole Frac. | Mole Frac. |
| $H_2$ | trace | 0.0000 | 0.0000 | 0.0000 | Trace |
| He | trace | 0.0001 | 0.0000 | 0.0000 | 0.0001 |
| $N_2$ | 0.0042 | 0.0009 | 0.0036 | 0.0034 | 0.0015 |
| $CO_2$ | 0.0368 | 0.0317 | 0.0317 | 0.0370 | 0.0375 |
| $H_2S$ | 0.0012 | 0.0000 | 0.0000 | 0.0000 | Trace |

Example 6

The inventors tested a variety of solutions to determine whether there was a freezing point depression, and whether a heat reaction occurred, and the final pH. The freezing point and temperature reached during reaction of the two components, for each solution, are outlined in

TABLE 36

| Final volume % Stabitrol ™ | Final volume % MEA | Heat reaction Temp (° F.) | Freezing Point (° C.) | pH |
|---|---|---|---|---|
| 10 | 50 | 140 | <-48 | 10.6 |
| 15 | 50 | 160 | <-48 | 10.1 |
| 7.5 | 37.5 | 140 | -42 | 10.3 |
| 2.5 | 50 | 100 | <-48 | 11.1 |
| 7.5 | 25 | ND | -23 | 10.4 |

Over a wide range of concentrations of Stabitrol™ and MEA, a depression of freezing point, and a heat reaction were observed.

We claim:

1. A solution for removing a sulphur compound or carbon dioxide from a fluid, said solution comprising:
   (a) sulphuric acid, at between about 0.1 to 4 percent by volume of the solution;
   (b) a metal, at between about 0.05 to 10 percent by weight of the solution;
   (c) an amine, at between about 10 to 80 percent by volume of the solution; and
   (d) water.

2. The solution of claim 1 wherein the sulphur compound is selected from a group consisting of: hydrogen sulphide, methyl mercaptan, ethyl mercaptan, n-propyl mercaptan, iso-butyl mercaptan and carbonyl sulphide.

3. The solution of claim 1 wherein the metal is selected from a group consisting of: copper, zinc, iron, magnesium or manganese.

4. The solution of claim 1 wherein the metal is copper.

5. The solution of claim 1 wherein the metal is zinc.

6. The solution of claim 1 wherein the amine is a primary amine.

7. The solution of claim 1 wherein the amine is selected from a group consisting of: monoethanolamine, diglycolamine, methyldiethanolamine.

8. The solution of claim 1 wherein the amine is a mixture of amines.

9. The solution of claim 1 wherein the sulphuric acid is present at between about 0.1 to 2 percent by volume of the solution.

10. The solution of claim 9 wherein the metal is present at between about 1 to 5 percent by weight of the solution.

11. The solution of claim 10 wherein the amine is present at between about 25 to 50 percent by volume of the solution.

12. A method of removing a sulphur compound or carbon dioxide from a fluid, comprising:
    (a) preparing a solution according to any one of the above claims, and
    (b) contacting the fluid with the solution.

13. The method of claim 12 wherein the sulphur compound is selected from a group consisting of: hydrogen sulphide, methyl mercaptan, ethyl mercaptan, n-propyl mercaptan, iso-butyl mercaptan and carbonyl sulphide.

14. The method of claim 12 wherein the fluid is a gas.

15. The method of claim 12 wherein the fluid is a liquid.

16. The method of claim 14 wherein the gas is natural gas.

17. The method of claim 14 wherein the gas is air.

18. The method of claim 15 wherein the liquid comprises a liquid hydrocarbon.

19. The method of claim 15 wherein the liquid is drilling mud.

20. The method of claim 12 practiced at a temperature of between about 0° C. and −51° C.

21. The method of claim 12 practiced at a temperature of between about −10° C. and 40° C.

22. A method of removing a sulphur compound or carbon dioxide from a gas, which method comprises:
    (a) preparing a solution according to any one of the above claims, and
    (b) contacting the gas with the solution,
    and characterized in that the method is performed at a temperature of between about 0° C. and −51° C.

23. The method of claim 22 performed at a temperature of between about −10° C. and 40° C.

24. The method of claim 22 performed at a temperature of between about −20° C. and 40° C.

25. The method of claim 22 performed at a temperature of between about −10° C. and −30° C.

26. The solution of claim 1, wherein the sulphuric acid is present at between about 1 to 4 percent by volume of the solution.

27. The solution of claim 1, wherein the sulphuric acid is present at about 2 percent by volume of the solution.

28. The solution of claim 1, wherein the sulphuric acid is present at about 2.3 percent by volume of the solution.

29. The solution of claim 1, wherein the solution has a pH of between about 8 and 12.

* * * * *